United States Patent
Singh (10) Patent No.: US 9,750,479 B2
(45) Date of Patent: *Sep. 5, 2017

(54) THREE-DIMENSIONAL X-RAY CT CALIBRATION AND VERIFICATION APPARATUS AND METHOD

(71) Applicant: Hexagon Metrology, Inc., North Kingstown, RI (US)

(72) Inventor: Gurpreet Singh, Providence, RI (US)

(73) Assignee: Hexagon Metrology, Inc., North Kingstown, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,432

(22) Filed: Jun. 27, 2014

(65) Prior Publication Data

US 2015/0374327 A1    Dec. 31, 2015

(51) Int. Cl.
*A61B 6/03* (2006.01)
*A61B 6/00* (2006.01)
*G01N 23/04* (2006.01)

(52) U.S. Cl.
CPC .............. *A61B 6/582* (2013.01); *A61B 6/03* (2013.01); *A61B 6/035* (2013.01); *A61B 6/583* (2013.01); *G01N 23/046* (2013.01)

(58) Field of Classification Search
CPC ......... A61B 6/035; A61B 6/582; A61B 6/583; A61B 6/584; A61B 8/587
See application file for complete search history.

(56) References Cited

U.S. PATENT DOCUMENTS

| 5,442,674 A | 8/1995 | Picard et al. .................... 378/20 |
| 5,636,255 A | 6/1997 | Ellis ................................. 378/20 |
| 5,793,835 A | 8/1998 | Blanck .............................. 378/4 |

(Continued)

FOREIGN PATENT DOCUMENTS

| FR | 2 700 909 | 7/1994 | ............... H04N 5/32 |
| WO | WO 2012/150336 | 11/2012 | ............... A61B 6/00 |
| WO | WO 2012/150336 A1 | 11/2012 | ............... A61B 6/00 |

OTHER PUBLICATIONS

Seifert et al., Visualization of x-ray microtomography data for a human tooth atlas, May 2004, Proc. SPIE, Medical Imaging, vol. 5367, p. 747, 749.*

(Continued)

*Primary Examiner* — Glen Kao
(74) *Attorney, Agent, or Firm* — Sunstein Kann Murphy & Timbers LLP (57) ABSTRACT

An apparatus for calibrating an x-ray computed tomography device has a plurality of objects formed from a material that is visible to x-rays. The plurality of objects are configured to receive x-rays without changing shape, and have substantially the same shape. The objects each have an object attenuation value to x-rays and a center point such that they are symmetrically shaped relative to their respective center points. The apparatus also has a base at least in part fixedly supporting the plurality of objects so that each of the plurality of objects contacts at least one of the other objects. Like other physical objects, such as the objects, the base has a base attenuation value to x-rays, and that value is greater than the base attenuation value. The center points of the plurality of objects together form a three-dimensional volume.

28 Claims, 8 Drawing Sheets

(56) References Cited

U.S. PATENT DOCUMENTS

| | | | |
|---|---|---|---|
| 5,963,612 A * | 10/1999 | Navab | A61B 6/4441 378/17 |
| 6,052,611 A * | 4/2000 | Yanof | A61B 90/10 378/207 |
| 6,364,529 B1 | 4/2002 | Dawson | 378/207 |
| 7,569,829 B2 | 8/2009 | Chen et al. | 250/363.09 |
| 7,697,738 B2 | 4/2010 | Da Silva et al. | 382/128 |
| 7,738,624 B2 | 6/2010 | Herold et al. | 378/18 |
| 8,000,442 B2 | 8/2011 | Lachaine et al. | 378/65 |
| 8,309,910 B2 | 11/2012 | Dutta et al. | 250/252.1 |
| 8,764,290 B2 | 7/2014 | O'Hare et al. | 378/207 |
| 8,777,485 B2 | 7/2014 | Holt | 378/207 |
| 8,911,149 B2 | 12/2014 | O'Hare et al. | 378/207 |
| 2003/0058999 A1 | 3/2003 | Mitschke et al. | 378/207 |
| 2005/0094771 A1 | 5/2005 | Basu et al. | 378/207 |
| 2005/0154548 A1* | 7/2005 | Basel | G01B 11/002 702/94 |
| 2007/0122020 A1 | 5/2007 | Claus et al. | 382/131 |
| 2008/0075227 A1* | 3/2008 | Christoph | A61B 6/583 378/23 |
| 2008/0093544 A1* | 4/2008 | Wang | A61B 6/583 250/252.1 |
| 2013/0195239 A1 | 8/2013 | O'Hare et al. | 378/4 |
| 2014/0153694 A1 | 6/2014 | Suppes et al. | 378/62 |

OTHER PUBLICATIONS

International Searching Authority, International Search Report—International Application No. PCT/US2015/025395, dated Aug. 5, 2015, together with the Written Opinion of the International Searching Authority, 9 pages.

Ahn et al., "Least-Squares Orthogonal Distances Fitting of Circle, Sphere, Ellipse, Hyperbola, and Parabola," Pattern Recognition, vol. 34, Issue 12, pp. 2283-2303, Dec. 2001.

Bartscher et al., "Achieving Traceability of Industrial Computed Tomography," Proc. of ISMTII 2009, St. Petersburg, Russia, 6 pages, Jun. 29-Jul. 2, 2009.

Boas et al., "CT artifacts: Causes and Reduction Techniques," *Imaging in Medicine*, vol. 4, No. 2, pp. 229-240, Apr. 2012.

Dewulf et al., "Uncertainty Determination and Quantification for Dimensional Measurements with Industrial Computed Tomography," CIRP Annals—Manufacturing Technology, vol. 62, Issue 1, pp. 535-538, 2013.

Iso-Gum, "Evaluation of Measurement Data—Guide to the Expression of Uncertainty in Measurement," 134 pages, 2008.

Johnston et al., "Geometric Calibration for a Dual Tube/Detector Micro-CT System," Medical Physics, vol. 35, Issue 5, pp. 1820-1829, May 2008.

Kiekens et al., "Uncertainty Determination for Dimensional Measurements with Computed Tomography," Conference on Industrial Computed Tomography, Austria, pp. 183-190, Sep. 19-21, 2012.

Konstantinidis, "Evaluation of Digital X-ray Detectors for Medical Imaging Applications, Electro-optical and X-ray performance evaluation of novel digital X-ray detectors," Lambert Academic Publishing, 258 pages, 2012.

Kruth et al., "Computed Tomography for Dimensional Metrology," CIRP Annals—Manufacturing Technology, vol. 60, Issue 2, pp. 821-842, 2011.

Spath, "Least Squares Fitting of Spheres and Ellipsoids Using Not Orthogonal Distances," Mathematical Communications, vol. 6, pp. 89-96, 2001.

Weckenmann et al., "Assessment of Measurement Uncertainty Caused in the Preparation of Measurements Using Computed Tomography," XIX IMEKO World Congress—Fundamental and Applied Metrology, Lisbon, Portugal, pp. 1888-1892, Sep. 6-11, 2009.

Yang et al., "A Geometric Calibration Method for Cone Beam CT Systems," Medical Physics, vol. 33, Issue 6, pp. 1695-1706, Jun. 2006.

International Searching Authority, Notification of Transmittal of the International Search Report and The Written Opinion of the International Searching Authority, or the Declaration, PCT/US2013/023602, dated May 2, 2013, 9 pages.

International Searching Authority, Notification of Transmittal of the International Search Report and The Written Opinion of the International Searching Authority, or the Declaration, PCT/US2015/025395, dated Aug. 5, 2015, 9 pages.

* cited by examiner

THREE-DIMENSIONAL X-RAY CT CALIBRATION AND VERIFICATION APPARATUS AND METHOD

RELATED APPLICATION

This patent application is related to the following patent applications, which are incorporated herein, in their entireties, by reference and owned by the same assignee:

U.S. Provisional Patent Application 61/592,169, filed Jan. 30, 2012, entitled, "X-RAY COMPUTED TOMOGRAPHY DEVICE CALIBRATION AND VERIFICATION APPARATUS," and naming Jonathan J. O'Hare and Stephen Darrouzet as inventors, U.S. patent application Ser. No. 13/752,698, filed Jan. 29, 2013, entitled, "X-RAY COMPUTED TOMOGRAPHY DEVICE CALIBRATION AND VERIFICATION APPARATUS," and naming Jonathan J. O'Hare and Steven Darrouzet as inventors, and U.S. patent application Ser. No. 14/281,006, filed May 19, 2014, entitled, "X-RAY COMPUTED TOMOGRAPHY DEVICE CALIBRATION AND VERIFICATION APPARATUS," and naming Jonathan J. O'Hare and Stephen Darrouzet as inventors.

FIELD OF THE INVENTION

The invention generally relates to calibration devices and, more particularly, the invention relates to calibration of x-ray computed tomography devices/CT machines.

BACKGROUND OF THE INVENTION

Coordinate measuring machines (CMMs) are used for accurately measuring a wide variety of different types of work pieces. For example, CMMs can measure critical dimensions of aircraft engine components, surgical tools, and gun barrels. Precise and accurate measurements help ensure that their underlying systems, such as an aircraft in the case of aircraft components, operate as specified.

Inaccurate measurements can have catastrophic effects. Accordingly, to ensure that CMMs deliver accurate measurements, the CMM industry has developed well-defined accuracy verification standards, procedures, and gauging tools to calibrate and verify the underlying machines taking these measurements. To those ends, a CMM verification procedure typically requires hard gauges that are traceable for uncertainty calculations, and designed in such a way to ensure that they (i.e., the gauges) are dimensionally stable.

More recently, those in the art have begun using computed tomography (CT) systems as CMMs for dimensional metrology. Undesirably, however, many such CT systems known to the inventors lack both well-defined verification standards, as well as gauging tools designed for that purpose.

SUMMARY OF VARIOUS EMBODIMENTS

In accordance with one embodiment of the invention, an apparatus for calibrating an x-ray computed tomography device has first, second, and third spheres formed from a material that is visible to x-rays. The spheres are configured to receive x-rays without changing shape, and each of the spheres has a sphere attenuation value to x-rays. The apparatus also has a base at least in part supporting the spheres so that each of the spheres contacts at least one of the other spheres. Like any other physical object, the base has a base attenuation value to x-rays. The sphere attenuation value is greater than the base attenuation value, and each of the spheres is locked in place on the base in a manner that prevents sphere translational movement. Preferably, the second sphere contacts the first and third spheres. Like any sphere, the first sphere has a first center, the second sphere has a second center, and the third sphere has a third center. In a corresponding manner, the first and second centers form a first line, and the first and third centers form a second line that diverges from the first line (i.e., they intersect).

The apparatus may include a fourth sphere contacting the first, second and third spheres. For example, the fourth sphere, which has a fourth center, may form a third line with the first center. This first line and the third line may form a plane that intersects the second line. Moreover, the fourth sphere may contact both the first and second spheres, but not contact the third sphere.

The first, second, and third spheres can be kinematically locked together, or secured together with an adhesive, and the base may have a stem with an orientation mark. In some embodiments, the first sphere contacts the third sphere. Although not necessary, the first, second, and third spheres preferably are dimensionally identical (e.g., each may have a precision to at least 0.01 millimeters). Among other materials, the first, second, and third spheres may, in one implementation, be formed at least in part from at least one of sapphire and ruby material.

In illustrative embodiments, the first, second and third spheres are precision ground or lapped spheres. In fact, each of the first, second, and third spheres may include a calibration certification of at least one of its dimensional properties (e.g., its diameter).

Each of the first, second, and third spheres preferably is a free-standing sphere (i.e., an independent sphere when not part of the apparatus).

In accordance with another embodiment, an apparatus for calibrating an x-ray computed tomography device has a plurality of objects formed from a material that is visible to x-rays. The plurality of objects are configured to receive x-rays without changing shape, and have substantially the same shape. The objects each have an object attenuation value to x-rays and a center point such that they are symmetrically shaped relative to their respective center points. The apparatus also has a base at least in part fixedly supporting the plurality of objects so that each of the plurality of objects contacts at least one of the other objects. Like other physical objects, such as the objects, the base has a base attenuation value to x-rays, and that value is greater than the object attenuation value. In one implementation, the center points of the plurality of objects together form a three-dimensional volume.

In accordance with other embodiments of the invention, a method of calibrating or verifying the dimensional accuracy of an x-ray computed tomography machine provides an x-ray computed tomography machine having calibration settings, and uses the x-ray computed tomography machine to image a gauge to produce a gauge reconstruction. The gauge has first, second, and third spheres visible to x-rays, and each sphere is in contact with at least one other sphere. The centers of the first and second spheres form a first line, while the centers of the first and third spheres form a second line that diverge from the second line. The method also measures, in the gauge reconstruction, the distance between at least two of the spheres to produce measured center distance values, and compares the measured center distance values against the known calibrated center distance values. Finally, the method uses the comparison to determine if there is a distance error in the gauge reconstruction.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, an apparatus for calibrating (or verifying) an x-ray computed tomography machine in two or three dimensions enables more accurate measurements of a work piece. Such an apparatus can be scaled for precise measurements of smaller dimensions of the work piece (e.g., in the sub-millimeter level, such as to the micrometer or nanometer level). To that end, the apparatus has a base that supports a plurality of precisely defined/specified objects oriented so that their precise measurement points (e.g., the centers of spheres) form a two-dimensional area or a three-dimensional volume. These areas or volumes are reconstructed and measured to calibrate the x-ray computed tomography machines. Details of illustrative embodiments are discussed below.

Figure 1A:
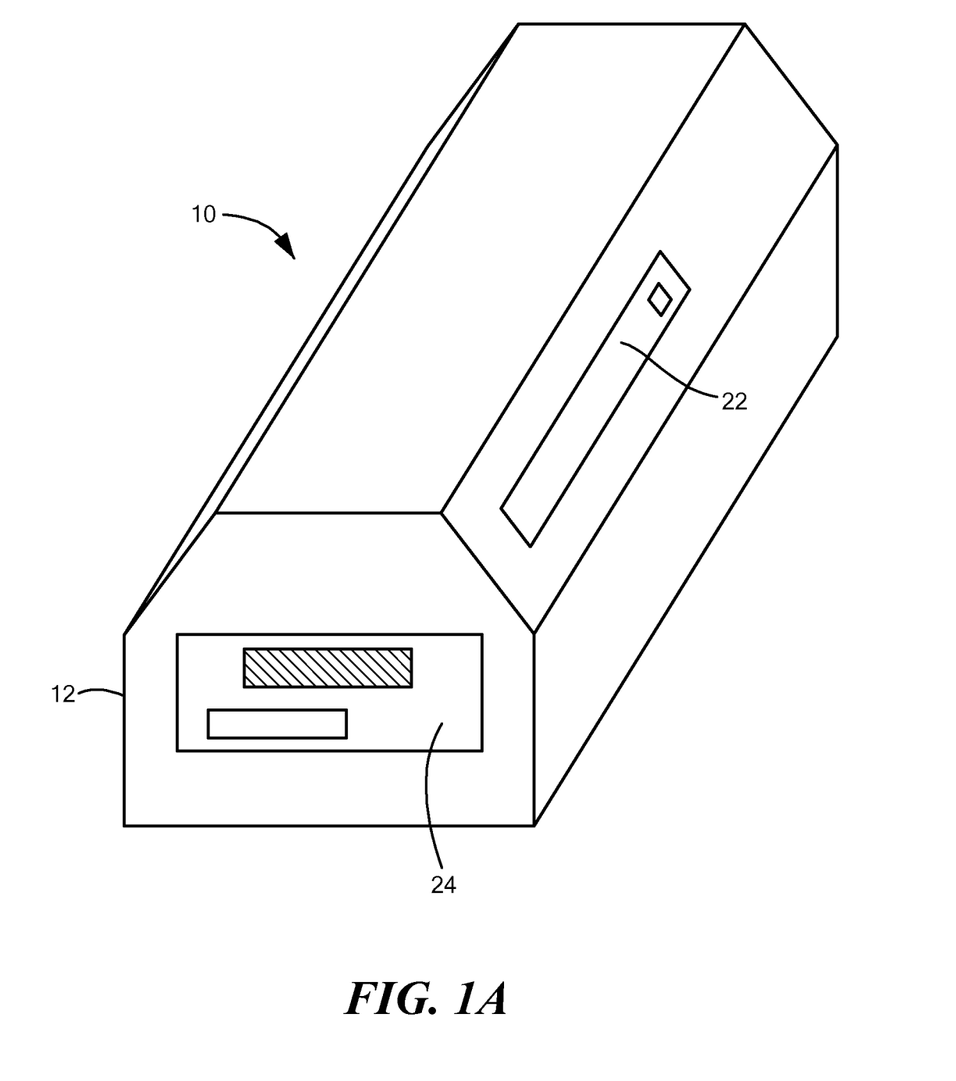
FIG. 1A schematically shows an x-ray computed tomography device that may use illustrative embodiments of the invention.
Figure 1B:
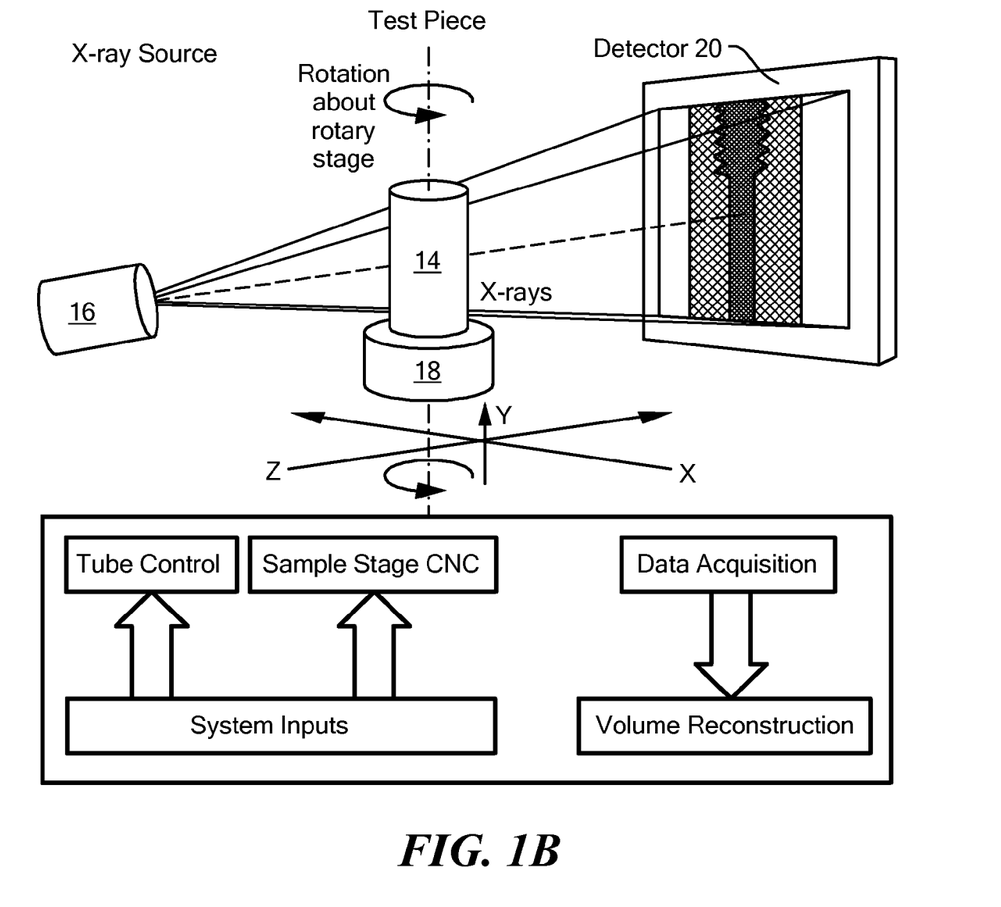
FIG. 1B schematically shows internal components of the device of FIG. 1A.

FIGS. 1A and 1B schematically show an x-ray machine/computer tomography device 10 that may use a calibration gauge configured in accordance with illustrative embodiments. It should be noted that although this discussion primarily relates to calibration, principles of various embodiments apply to verification of the accuracy of x-ray computed tomography devices 10. Accordingly, discussion of calibration is not intended to limit all embodiments of the invention.

Among other things, the x-ray computed tomography machine 10 may be a computed tomography system (a/k/a a "CT system" or a CT machine) that produces a three dimensional model of a work piece within its interior (referred to as a "work piece reconstruction"). To those ends, the x-ray computed tomography machine 10 has a housing 12 forming an interior chamber for containing, among other things (see FIG. 1B):

a work piece 14 to be measured,
an x-ray gun 16 for generating x-rays,
a rotary stage 18 for rotating the work piece 14, and
a detector 20 for detecting the image/projection of the work piece 14 after it is imaged by the x-ray gun 16.

An access door 22, which may be made from a transparent material, provides access to the interior for adding and removing work pieces 14. For example, the work piece 14 may be a cardiovascular stent commonly used in coronary angioplasty procedures, or a propeller used with a military ship (e.g., an air craft carrier). A control panel 24 on the side of the machine 10 acts as the control interface for an operator.

To produce the 3D model of the work piece 14 (the "reconstruction"), the computed tomography machine 10 effectively moves the work piece 14 relative to the x-ray guns 16. For example, the computed tomography machine 10 may rotate the work piece 14 a full 360 degrees on the rotary stage 18, and take multiple x-ray images (known in the art as "projections" or "projection angles") of the work piece 14 during rotation. During and/or after rotating the work piece 14, a model building module (e.g., post-processing software executing on a local microprocessor or microcontroller) converts the data of all the projections into a 3D model of the work piece 14—i.e., the noted reconstruction. It is this 3D model—which may be a software model—that may be measured to confirm the dimensional accuracy of the work piece 14. Thus, if the work piece 14 is a small medical device, such as a cardiovascular stent, then measurement software may precisely measure selected features of the stent, such as its radius, wall thickness, etc.

If the computed tomography machine 10 is not properly calibrated, however, then these work piece measurements likely will be inaccurate. Some inaccuracies are acceptable, while others may be beyond tolerances. Accordingly, the operator or some other person should calibrate the computed tomography machine 10 prior to use. Undesirably, however, the inventors know of no highly reliable and efficient technique on the market to calibrate conventional computed tomography machines in multiple dimensions. To fill that deficiency in the art, the inventors have developed a highly accurate, fine pitch calibration gauge.

Figure 2A:
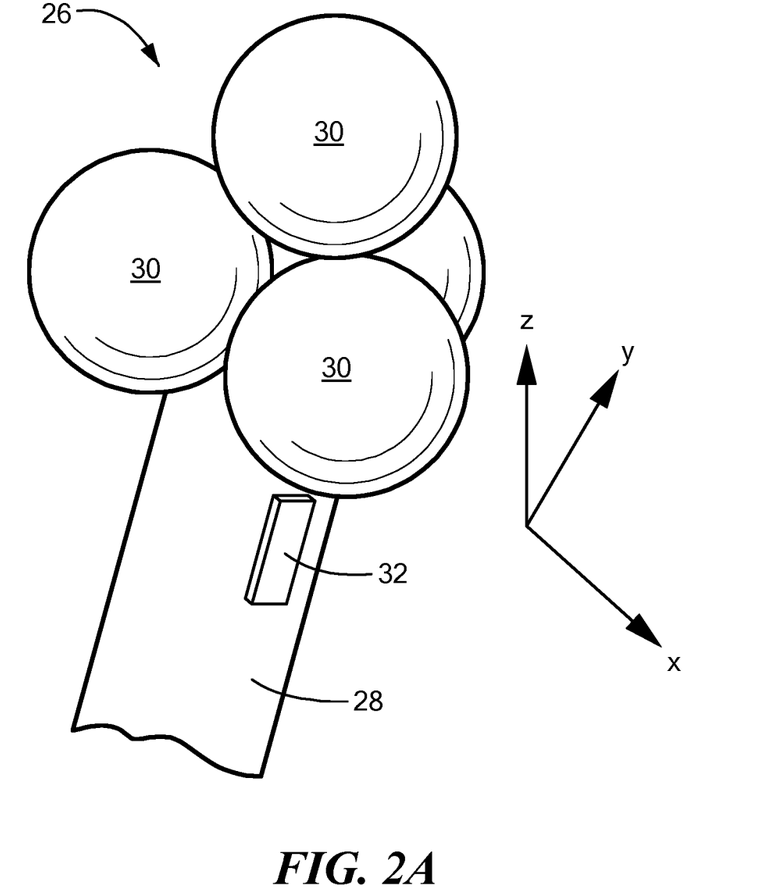
FIG. 2A schematically shows a perspective view of an x-ray calibration and verification gauge configured in accordance with illustrative embodiments of the invention.

Specifically, FIG. 2A schematically shows an illustrative gauge 26 for calibrating or verifying a computed tomography machine 10, such as that shown in FIGS. 1A and 1B. The gauge 26 has a base 28 that supports a plurality of discrete objects 30 that act as guideposts in the calibration process. More specifically, in illustrative embodiments, the objects 30 preferably comprise three or more spheres (four spheres in this example and identified by reference number "30") that are ground or lapped to have very precise qualities (precise symmetry, shape, size, volumes, centers, geometry, etc.). In illustrative embodiments, the spheres 30 are certified by some reliable and well-known third party to have certain prescribed measurement qualities. Each of the spheres 30 is a free-standing and independent structure—they preferably are not integral to or even connected to each other in one arrangement. Instead, the spheres 30 merely contact each other. As discussed in greater details below, some embodiments position the spheres 30 so that their centers form a plane or a volume.

The base 28 supports the spheres 30. More specifically, in the embodiment shown in FIG. 2A, the base 28 is a carbon fiber stem that supports four spheres 30 generally oriented in a pyramidal structure/pyramid. One or both faces of the base 28 have an orientation mark 32, formed from a material that is visible to x-rays. This orientation mark should enable the user to see the gauge orientation; more specifically, it should identify similarly sized spheres and apply the calibrated values to the correctly identified sphere on an x-ray reconstruction.

From the orientation of the figures, the pyramid has three spheres 30 on the bottom and one sphere 30 on the top. The spheres 30 preferably are constrained so that they cannot move translationally relative to the base 28 or translationally relative to each other—i.e., in a direction relative to the X-axis, Y-axis, or Z-axis. Some embodiments also are constrained so that the spheres 30 cannot move in any other manner, e.g., they cannot rotate relative to the base 28. Other embodiments, however, may permit non-translational motion, such as rotation relative to the base 28.

In the ideal case, each sphere 30 only contacts its neighboring sphere(s) 30 at an infinitesimally small, discrete point. This ensures that the spheres 30 are minimally constrained, thus providing maximum stability. In more simplified terms, if it is minimally constrained, then a sphere 30 should not rock or otherwise linearly move relative to other spheres 30—it is substantially immovable during normal operation (absent application of an unusual force). Indeed, in actual use, the spheres 30 cannot contact at infinitesimally small points. In other words, the point of contact of the spheres 30 has a minimal amount of surface area.

Those skilled in the art can drive toward this idealized point contact, however, by using the more finely and accurately produced spheres 30. The spheres 30, which preferably are free-standing and independent, thus may be formed to have a very fine precision. For example, the spheres 30 may have a diameter with a precision to at least 0.01 millimeters. Specifically, a precision of at least 0.01 millimeters may have an even finer precision, such as 0.001 millimeters, 0.005 millimeters, 0.0001 millimeter, 0.00001 millimeters, etc. As another example, the spheres 30 may have a diameter of 10.0001 millimeters, within some known tolerance, such as 0.00005 millimeters. All spheres 30 of the same gauge 26 may be the same size, or different sizes. In either case, the diameters of the spheres 30 are known to the noted precision. Accordingly, illustrative embodiments can detect a variance of the reading by the CT machine 10 by an amount on the order of the precision of the sphere 30—down to the micrometer or nanometer level. The spheres 30 preferably include a certification from a reliable certification authority of their properties (e.g., dimensional properties).

Illustrative embodiments secure the spheres 30 to the base 28 by conventional means. For example, the gauge 26 may have adhesive or other features that secure the spheres 30 to the base 28. Other embodiments, discussed herein, do not require such means and may simply be retained by an effective kinematic lock.

To calibrate the computed tomography machine 10, a calibration module (not shown) measures the distance between identifiable regions of the objects 30. For example, in the sphere embodiment, the calibration module may measure between the centers of the spheres 30. If the object 30 was not in the form of a sphere 30 (e.g., in the form of a protrusion, cube, cylinder, irregular shape, etc.), then the identifiable region could be the center of that shaped object 30, or some other area of that object 30, such as an end, a discontinuity, a corner, the intersection of two portions, etc. Even if the objects 30 are spheres 30, the identifiable portion could be an exterior region of the spheres 30.

Accordingly, it is important for the spheres 30 to be visible on the x-ray images. To that end, the spheres 30 preferably are formed from a material having a higher attenuation to x-rays than the attenuation of the base 28. For example, the spheres 30 may be formed from ruby, sapphire, or other material for the purpose of providing low thermal expansion and x-ray attenuation near the middle of the range of intensity values of the computed tomography machine 10. Indeed, those skilled in the art can select other materials having the desired properties.

Among other things, the base 28 may be formed from a carbon fiber (as noted above) with a high stiffness. In preferred embodiments, the carbon fiber has an x-ray attenuation that is relatively low when compared to the material of the spheres 30. This differential in attenuations should provide good contrast and a clear separation between the surfaces of interest (i.e., the spheres 30) and the base 28. In a manner similar to the spheres 30, those in the art should understand that the base 28 may be formed from another material having similar properties. In illustrative embodiments, the coefficient of thermal expansion of the spheres 30 and base 28 is as low as possible, such as no greater than that for steel.

As noted, the spheres 30 permit a user to calibrate the underlying computed tomography machine 10 in one, two, or three dimensions. Unlike the prior art devices, there is no need to execute a complete scan of the gauge 26, and then reposition the gauge 26 to scan in another direction. Instead, illustrative embodiments permit a user to fully calibrate the computed tomography machine 10 without the necessity of repositioning the gauge 26. The gauge 26 thus has measurable structure in at least two or three dimensions. For example, the gauge 26 may have measurable structure in the X and Y planes, or in the X, Y, and Z planes. Accordingly, the gauge 26 may be considered to form measurable areas or volumes that facilitate those measurements.

Figure 2B:
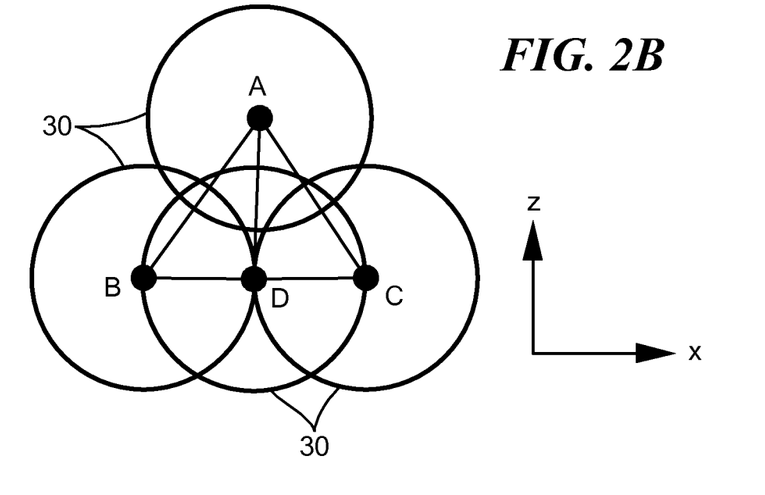
FIG. 2B schematically shows a side projection of the verification objects of the gauge shown in FIG. 2A.
Figure 2C:
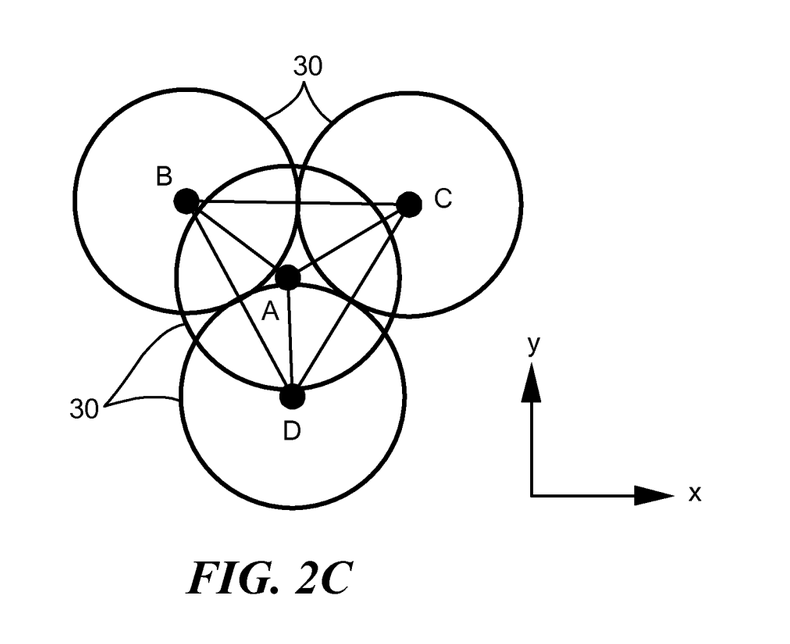
FIG. 2C schematically shows a top projection of the verification objects of the gauge shown in FIG. 2A.

To those ends, in this embodiment, the center of each sphere 30 may be considered to form a straight line with the center point of each of the other spheres 30. FIG. 2B schematically shows a straight-on side projection of the four spheres 30 of FIG. 2A, while FIG. 2C schematically shows a straight-on top projection of the four spheres 30 of FIG. 2A.

The centers of the spheres 30 are identified in these drawings as points A, B, C, and D. The centers form six straight lines: A-B, A-C, A-D, B-C, B-D, and C-D, which are shown in FIGS. 2B and 2C. As shown, each line segment intersects with/diverges from at least one other line segment—in this case, all line segments intersect with/diverge from all of the other line segments. In other words, while not necessary, not one of the line segments is parallel to the other line segments.

Moreover, as noted above, these diverging line segments combine to form measurable areas and volumes, effectively forming two-dimensional or three dimensional gauges 26. For example, as shown in the top view of FIG. 2C, lines B-C, C-D, and B-D together form a triangular area that is generally orthogonal with the Z-axis. This triangular area permits calibration and verification in the X and Y dimensions; i.e., two-dimensional calibration, without the necessity of moving the gauge 26 for a second scan (discussed below). In fact, some embodiments omit the top sphere 30 and simply use three spheres 30 for two-dimensional calibration and verification. Either way, this embodiment forms a two-dimensional gauge 26.

In a similar manner, this triangular area forms a pyramidal volume when the points B, C, and D form lines with point A of the top sphere. FIG. 2B more clearly shows the depth of this volume in the Z-direction. These three additional diverging lines thus permit calibration and verification in the X-direction, Y-direction, and Z-direction, effectively forming a three-dimensional gauge 26.

Figure 3:
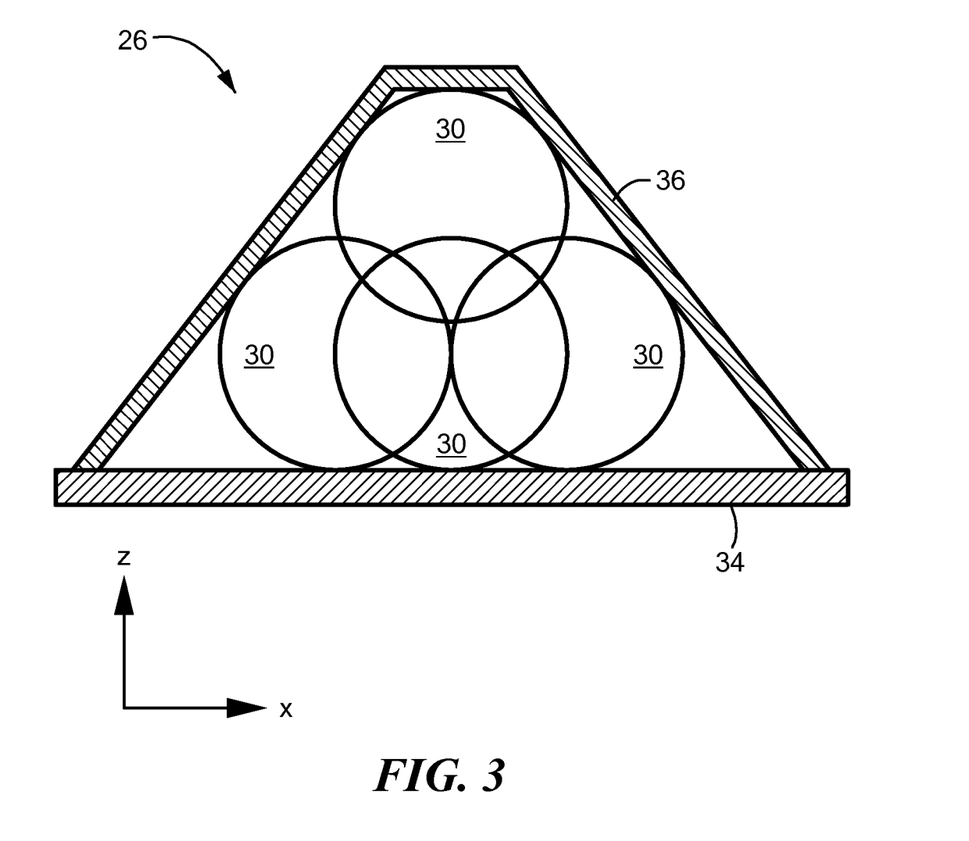
FIG. 3 schematically shows a side view of an x-ray calibration and verification gauge configured in accordance with alternative embodiments of the invention.

Some embodiments have a different type of base 28. Specifically, rather than using the stem 28, such embodiments may have a relatively stiff and thermally stable support plate 34 that is minimally visible to x-rays.

FIG. 3 schematically shows one embodiment of such an arrangement using a support plate 34 and an optional securing member 36. As with other embodiments, the support plate 34 and securing member 36 preferably are minimally visible to x-rays. This embodiment can kinematically lock the spheres 30 in place by normally applying a force to the spheres 30 in all three dimensions. In a manner similar to the sphere-to-sphere contact, the securing member 36 ideally contacts the spheres 30 at no more than one point.

In this kinematically locked configuration, the spheres 30 do not require any other means to keep them in contact and immobile. In other words, no adhesive, fasteners or other means is necessary to maintain the sphere 30 in the proper position. Such extra components undesirably could impact the actual position of the spheres 30, or impede visualization of the spheres 30 under the x-rays. Other embodiments, however, may have such additional components.

Figure 4:
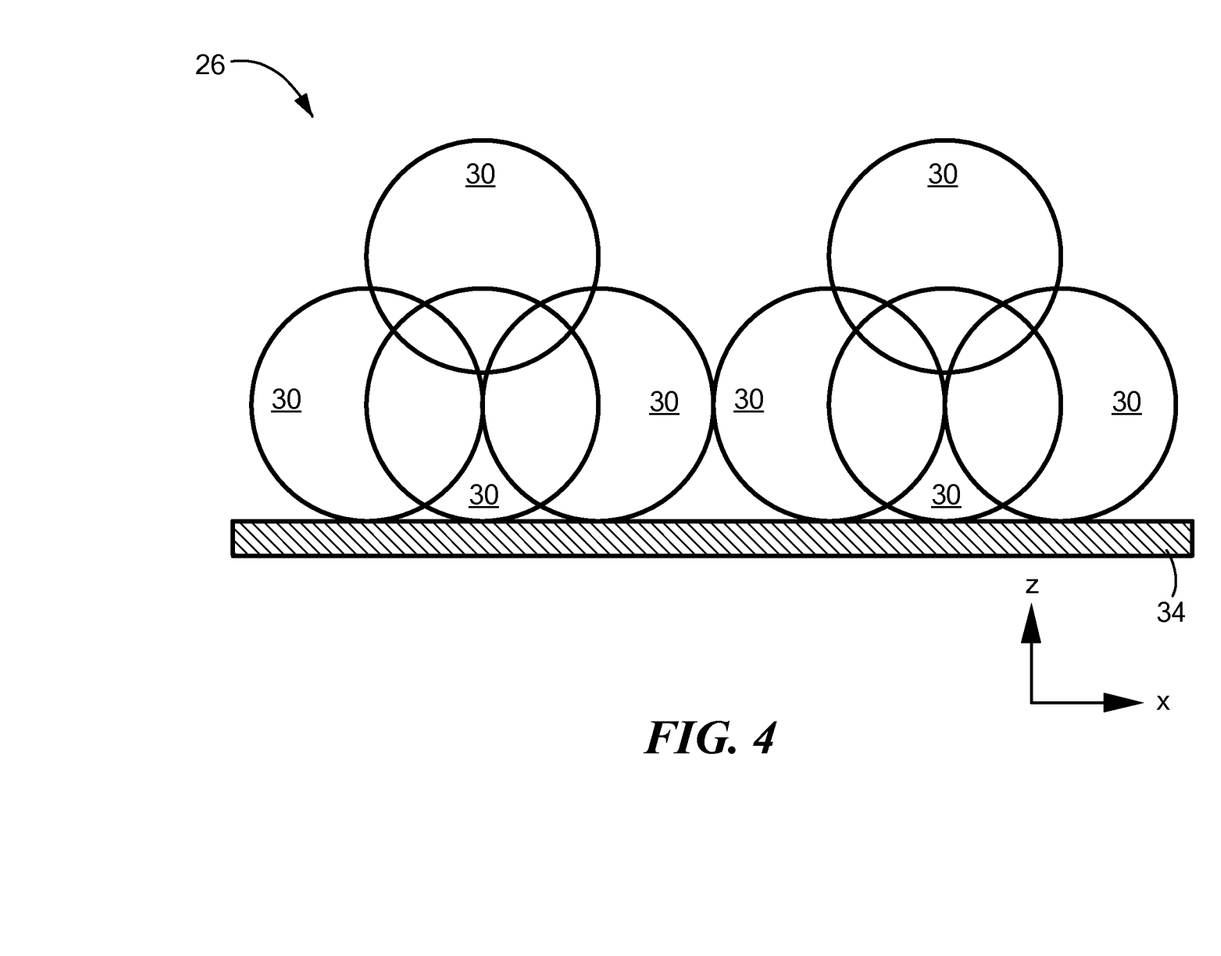
FIG. 4 schematically shows an x-ray calibration and verification gauge configured in accordance with further embodiments of the invention.

The gauge structure preferably is scalable and can be sized appropriately for measuring larger volumes. For example, the size, number, and arrangement of spheres 30 can be revised to meet the evolving computed tomography standards, which dictate a certain minimum percentage coverage of the total measurement volume. FIG. 4 schematically shows a side view of one such embodiment, in which two sets of four spheres 30, like those shown in FIG. 3, are formed side-by-side on a support plate 34. Although not shown, this embodiment can include a securing member 36, or remain free of the securing member 36.

Figure 5:
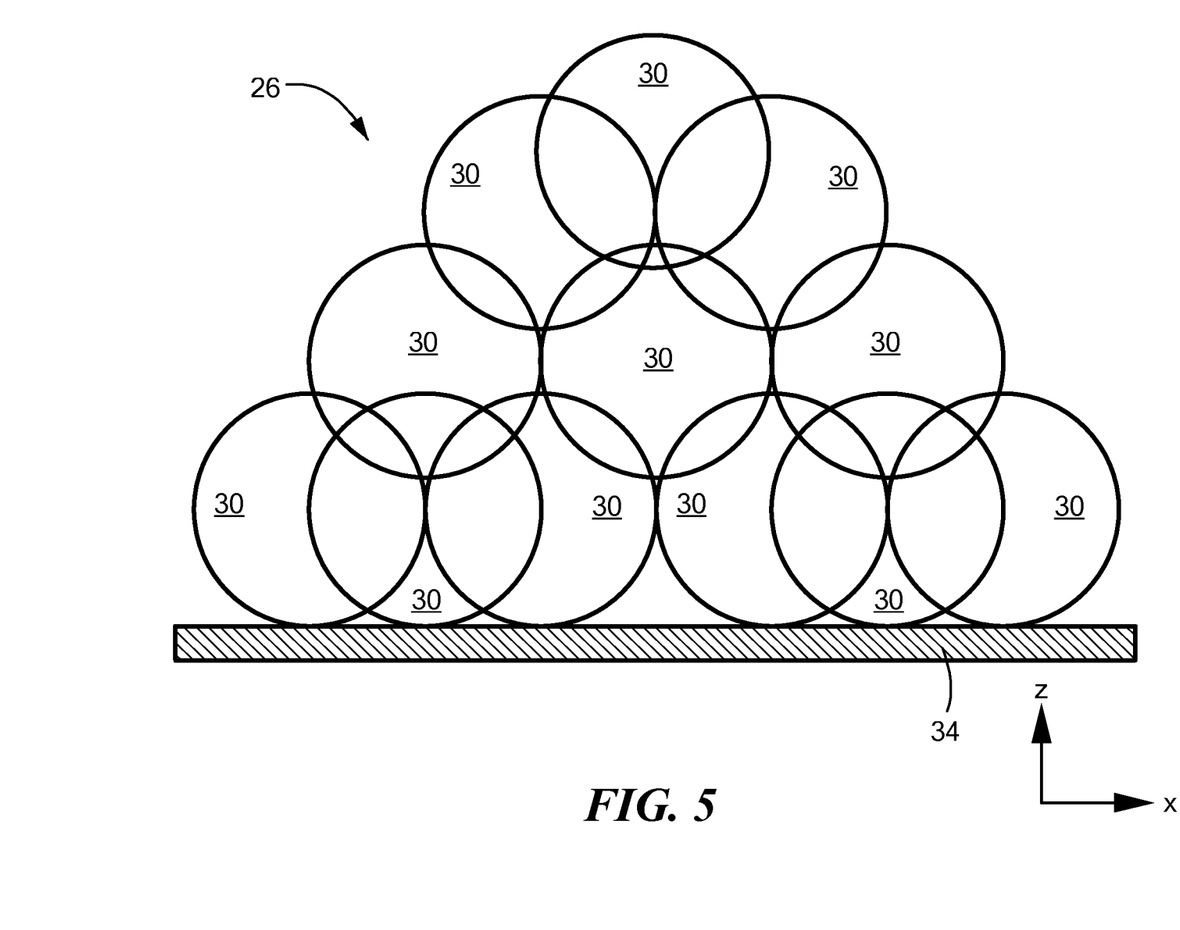
FIG. 5 schematically shows an x-ray calibration and verification gauge configured in accordance with still other embodiments of the invention.

To form an even larger gauge 26 on a support plate 34, FIG. 5 schematically shows a side view of a similar embodiment using three sets of spheres 30 arranged as in FIG. 3. This embodiment forms a pyramid-like structure, but without a top sphere 30. Some embodiments may add another sphere 30, however, to form a single measurement point on the top of the pyramid. Again, like the embodiments of FIGS. 3 and 4, this embodiment can have an optional securing member 36. Another common feature of the embodiments of FIGS. 3 and 4, and unlike that of FIG. 2, is the fact that no sphere 30 contacts all of the spheres 30 of the gauge 26.

Figure 6:
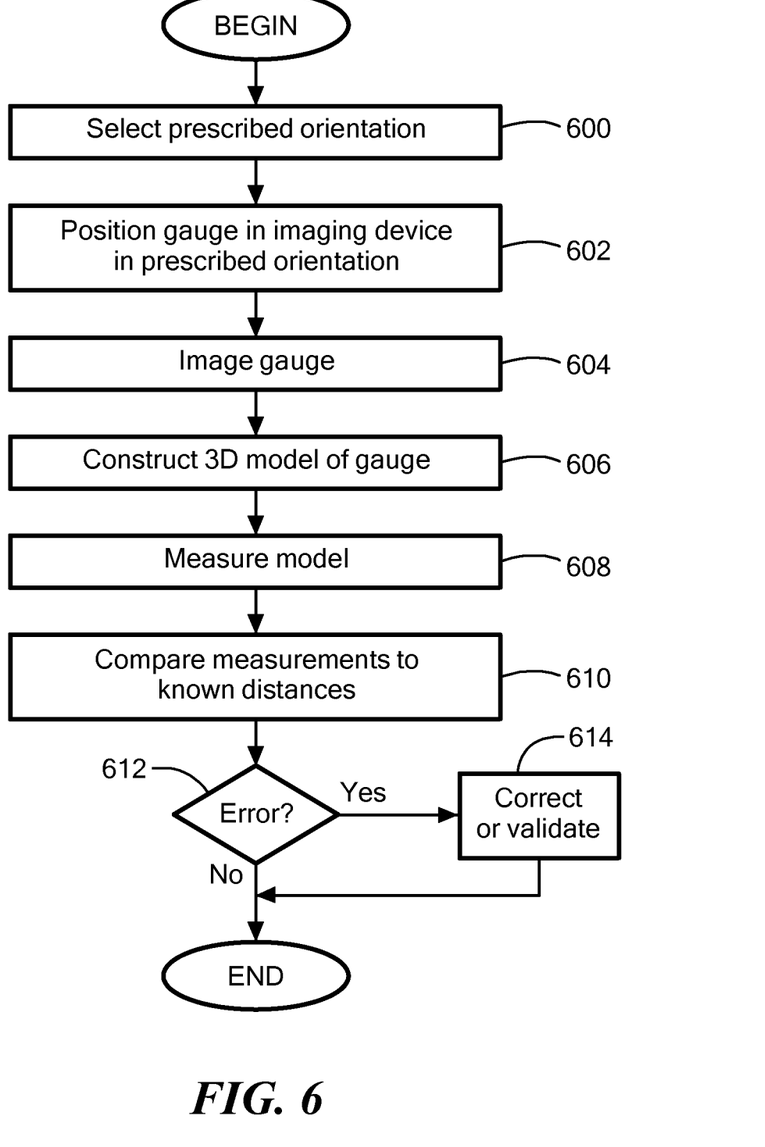
FIG. 6 shows a process of using the gauge of FIG. 2A in the x-ray computed tomography device of FIG. 1.

FIG. 6 shows a process of using the gauge 26 in accordance with one embodiment of the invention. The process begins at step 600 by selecting a prescribed orientation for the gauge 26 within the x-ray computed tomography machine 10. For example, if the gauge 26 calibrates/verifies in two-dimensions, then the operator may orient the gauge 26 to be parallel with the plane formed by the X-Y axes, or the planed formed by the Z-X axes. If the gauge 26 calibrates/verifies in three dimensions, however, then the operator may orient the three-dimensional gauge 26 in any random orientation.

Next, the process physically positions the gauge 26 within the x-ray computed tomography machine 10 in the prescribed orientation (step 602) and images the gauge 26 (step 604). To that end, the gauge 26 may be positioned on the rotary stage 18, which preferably rotates the gauge 26 a full 360 degrees. During this time, the x-ray computed tomography machine 10 is taking sequenced images/projections of the gauge 26 for subsequent processing. In illustrative embodiments, this one scan can gather enough information to fully calibrate and verify the x-ray computed tomography machine 10 (e.g., in the case of a three-dimensional gauge 26). Other embodiments may require two scans (e.g., in the case of a two-dimensional gauge 26). Either way, this is a vast improvement over prior art one-dimensional gauges, which repeat the process for each dimension of the computed tomography machine 10.

After the x-ray computed tomography machine 10 finishes imaging the gauge 26, the process constructs a three-dimensional model ("3D model") of the gauge 26 (step 606). A model engine (or model building module) thus uses the data from the successive images to construct the 3D model—a gauge reconstruction, which can be stored in memory. Although not necessary, rendering software may render the 3D model, and then rotate or otherwise move the ultimate 3D model for a viewer, thus showing the details of the gauge 26.

Step 608 then measures the 3D model elements to determine if it is dimensionally accurate. To that end, the process measures between preselected points within the gauge reconstruction. For example, the process may measure from the centers of the spheres; e.g., from the center of one sphere 30 to the center of one or more of the other spheres 30. This step thus produces a plurality of distance values for verification in subsequent steps.

Specifically, the actual distance between the prespecified points is known; in preferred embodiments, those distances are certified. For example, the known distance between the centers of two spheres 30 of FIG. 5 can be 10.0001 millimeters. The known distance between the centers of two other spheres 30 in FIG. 5 could be 20.0002 millimeters.

Accordingly, step 610 compares those different measured distances against the known distances to determine if there are errors (step 612). For example, the process simply may determine the difference between the various measurements and the known distances. This difference is the calibration error of the computed tomography machine 10. Using the example above, if the measured distance between the first two spheres 30 (known distance 10.0001 millimeters) is 10.0004 millimeters, then the computed tomography machine 10 has an error of 0.0003 millimeters and thus, should be appropriately modified or adjusted.

Accordingly, if the process detects errors beyond some preset limits or tolerances (e.g., detecting this exemplary 0.0003 millimeter error), then step 614 corrects the error by refining the initial calibration settings of the computed tomography machine 10, concluding the process.

Illustrative embodiments therefore improve the calibration and verification process by requiring fewer scans, thus saving time and resources. Such embodiments calibrate and verify using fine pitch details in two or three dimensions, ultimately enabling more accurate measurements of a work piece 14.

Although the above discussion discloses various exemplary embodiments of the invention, it should be apparent that those skilled in the art can make various modifications that will achieve some of the advantages of the invention without departing from the true scope of the invention.

What is claimed is:

1. An apparatus for calibrating an x-ray computed tomography device, the apparatus comprising:
   first, second, and third spheres formed from a material that is visible to x-rays, the three spheres being configured to receive x-rays without changing shape, each of the three spheres having a sphere attenuation value to x-rays; and
   a base at least in part supporting the three spheres so that each of the spheres contacts at least one of the other spheres, the base having a base attenuation value to x-rays, the sphere attenuation value being greater than the base attenuation value, each of the spheres being locked in place on the base in a manner that prevents sphere translational movement, the second sphere contacting the first and third spheres, the first sphere having a first center, the second sphere having a second center, the third sphere having a third center, the first and second centers forming a first line, the first and third centers forming a second line, the first and second lines diverging, the first, second and third spheres being kinematically locked together.

2. The apparatus as defined by claim 1 further comprising a fourth sphere contacting the first, second and third spheres.

3. The apparatus as defined by claim 2 wherein the fourth sphere has a fourth center forming a third line with the first center, the first line and the third line forming a plane that intersects the second line.

4. The apparatus as defined by claim 1 wherein the base includes an orientation mark.

5. The apparatus as defined by claim 1 further comprising a fourth sphere in contact with the first and second spheres, the fourth sphere being not in contact with the third sphere.

6. The apparatus as defined by claim 1 wherein the first sphere contacts the third sphere.

7. The apparatus as defined by claim 1 wherein the first, second, and third spheres are dimensionally identical and each have a precision to at least 0.01 millimeters.

8. The apparatus as defined by claim 1 wherein the first, second, and third spheres comprise at least one of sapphire and ruby material.

9. The apparatus as defined by claim 1 wherein an adhesive secures the first sphere to the second sphere.

10. The apparatus as defined by claim 1 wherein the first, second, and third spheres are precision ground or lapped spheres.

11. The apparatus as defined by claim 1 wherein each of the first, second, and third spheres includes a certification of at least one of its dimensional properties.

12. The apparatus as defined by claim 1 wherein each of the first, second, and third spheres is a free-standing sphere.

13. The apparatus as defined by claim 1 wherein the base is configured to expose the first, second, and third spheres to the environment.

14. An apparatus for calibrating an x-ray computed tomography device, the apparatus comprising:
    a plurality of objects formed from a material that is visible to x-rays, the plurality of objects being configured to receive x-rays without changing shape, each of the plurality of objects having substantially the same shape, the objects each having an object attenuation value to x-rays, each of the plurality of objects having a center point and being symmetrically shaped relative to its center point; and
    a base at least in part fixedly supporting the plurality of objects so that each of the plurality of objects contacts at least one of the other objects, the base having a base attenuation value to x-rays,
    the object attenuation value being greater than the base attenuation value,
    the center points of the plurality of objects together forming a three-dimensional volume,
    the plurality of objects being kinematically locked together.

15. The apparatus as defined by claim 14 wherein the plurality of objects comprises a sphere.

16. The apparatus as defined by claim 14 wherein the plurality of objects are oriented in a pyramidal form.

17. The apparatus as defined by claim 14 wherein the base includes a stem with an orientation mark.

18. The apparatus as defined by claim 14 wherein the plurality of objects comprises four objects.

19. The apparatus as defined by claim 14 wherein the plurality of objects comprises at least one of sapphire and ruby material.

20. The apparatus as defined by claim 14 wherein an adhesive secures at least one object to the base.

21. A method of calibrating or verifying the dimensional accuracy of an x-ray computed tomography machine, the method comprising:
    providing an x-ray computed tomography machine having calibration settings;
    using the x-ray computed tomography machine to image a gauge to produce a gauge reconstruction, the gauge comprising first, second, and third spheres visible to x-rays, each sphere in contact with at least one other sphere, the first, second and third spheres being kinematically locked together, the centers of the first and second spheres forming a first line, the centers of the first and third spheres forming a second line, the first line diverging from the second line;
    measuring, in the gauge reconstruction, the distance between at least two of the spheres to produce measured center distance values;
    comparing the measured center distance values against known center distance values; and
    using the comparison to determine if there is a distance error in the gauge reconstruction.

22. The method as defined by claim 21 further comprising:
    modifying the calibration settings of the x-ray computed tomography machine if the comparison determines that there is a distance error in the gauge reconstruction.

23. The method as defined by claim 22 further comprising:
    determining the difference between each measured center distance value and the relevant known center distance value, modifying the calibration settings being a function of each difference.

24. The method as defined by claim 21 wherein using the x-ray comprises:
    producing a reconstruction of the gauge from a plurality of different projections, the method further comparing the measured center distance values of the spheres in each of the reconstruction against the respective known center distance values for calibrating the computed tomography machine.

25. The method as defined by claim 21 wherein measuring comprises measuring a 3D model of the gauge.

26. The method as defined by claim 21 wherein each of the spheres is identically sized.

27. The method as defined by claim 21 wherein the three or more of the spheres each have a precision to at least 0.01 millimeters.

28. The method as defined by claim 21 wherein measuring comprises measuring in at least two dimensions.

* * * * *